United States Patent
Ikemoto et al.

(10) Patent No.: US 11,035,835 B2
(45) Date of Patent: Jun. 15, 2021

(54) ANALYSIS METHOD

(71) Applicant: Mitsubishi Gas Chemical Company, Inc., Chiyoda-ku (JP)

(72) Inventors: Kazuto Ikemoto, Niigata (JP); Satoko Imaruoka, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/764,238

(22) PCT Filed: Dec. 19, 2018

(86) PCT No.: PCT/JP2018/046770
§ 371 (c)(1),
(2) Date: May 14, 2020

(87) PCT Pub. No.: WO2019/138817
PCT Pub. Date: Jul. 18, 2019

(65) Prior Publication Data
US 2020/0278331 A1 Sep. 3, 2020

(30) Foreign Application Priority Data
Jan. 12, 2018 (JP) .............................. JP2018-003636

(51) Int. Cl.
*G01N 30/88* (2006.01)
*G01N 30/06* (2006.01)
*G01N 33/03* (2006.01)

(52) U.S. Cl.
CPC ............ *G01N 30/88* (2013.01); *G01N 30/06* (2013.01); *G01N 33/03* (2013.01); *G01N 2030/067* (2013.01); *G01N 2030/884* (2013.01)

(58) Field of Classification Search
None
See application file for complete search history.

(56) References Cited

FOREIGN PATENT DOCUMENTS

JP 4-145360 A 5/1992
JP 2017-187321 A 10/2017

OTHER PUBLICATIONS

Kumazawa, Takeshi, "Study on determination of pyrroloquinoline quinine derivatives in various foods", Research Report for Grants-in-Aid for Scientific Research, May 23, 2012, total pp. 6.
Ando, Atsumasa et al., "LC—MS/MS analysis of pyrroloquinoline quinone (PQQ)", The Vitamin Society of Japan, Dec. 25, 2014, vol. 88, No. 12, pp. 601-609.

(Continued)

*Primary Examiner* — Daniel S Larkin
(74) *Attorney, Agent, or Firm* — Oblon, McClelland, Maier & Neustadt, L.L.P.

(57) ABSTRACT

An analysis method having: a sample preparation step of preparing a measurement sample by mixing a measurement object containing pyrroloquinoline quinone or a salt thereof with glycine so that the pyrroloquinoline quinone or the salt thereof reacts with the glycine to produce imidazopyrroloquinoline or a salt thereof; and a quantitative analysis step of determining quantitatively the amount of the pyrroloquinoline quinone and the salt thereof contained in the measurement object, based on a chromatogram of the imidazopyrroloquinoline or the salt thereof contained in the measurement sample obtained by chromatography.

10 Claims, 2 Drawing Sheets

(56) References Cited

OTHER PUBLICATIONS

Kumazawa, Takeshi et al., "Levels of pyrroloquinoline quinone in various foods", Biochem, J., Apr. 15, 1995, vol. 307, pp. 331-333.
Suizu, Tomoki et al., "Spectrophotometric Determination of Pyrroloquinoline quinone with N,N-Diethyl-p-phenylenediamine", Bunseki Kagaku, 2011, vol. 60, No. 7, pp. 599-602.
Ikemoto, Kazuto et al., "HPLC Analysis of Pyrroloquinoline Quinone in Capsules", Bunseki Kagaku, 2016, vol. 65, No. 6, pp. 339-342.
International Search Report dated Mar. 12, 2019 in PCT/JP2018/046770 filed on Dec. 19, 2018, 2 pages.

ANALYSIS METHOD

TECHNICAL FIELD

The present invention relates to a method for quantitative analysis of pyrroloquinoline quinone or a salt thereof.

BACKGROUND ART

Pyrroloquinoline quinone (hereinafter sometimes simply referred as PQQ) is a substance having an o-quinone structure in which a pyrrole ring and a quinoline ring are condensed. PQQ is known to function as an electron carrier, and can be incorporated into aminoadipate semialdehyde dehydrogenase (AAASDH), which is involved in the metabolism of the essential amino acid lysine, to enable the redox reaction of AASDH. That is, it is thought to be a coenzyme of AASDH. Therefore, it is evaluated as the third redox coenzyme next to nicotinamide (pyridine nucleotide) and flavin and may become a novel vitamin.

In addition, PQQ is thought to have many important physiological activities such as promoting cell growth activity, anti-cataract activity, preventing/treating liver disease activity, promoting wound healing activity, anti-allergic activity, reverse transcriptase inhibitory activity, glyoxalase I inhibitory activity and anticancer activity, and its usages have been increasing in industrial importance.

PQQ has been known to be widely present in bacteria and fungi such as molds and yeasts, but in recent years, it has been reported that it is present not only in bacteria but also widely ranging from plants such as rice, to mammals. PQQ has been also reported to be detected from various tissues and organs in mammals. However, since mammals do not have a synthetic pathway for PQQ, they are thought to ingest PQQ from foods.

For functional foods that utilizing the functionalities, it is required to obtain accurate measurement data of PQQ in food under the System for Foods with Functional Claims. Many foods are not provided as single food products but as products mixed with various substances. On the other hand, PQQ is prone to react with many food components and is subject to interference from the components during analysis. For an analysis scale, analysis of the content on the order of mg of PQQ contained in capsules or tablets is performed.

As analysis methods for PQQ, gas chromatography/mass spectrometry (Patent Literature 1) and liquid chromatography/tandem mass spectrometer (Patent Literature 2) have been previously reported. However, these analysis methods are optimized for trace analysis such as analysis on the order of ng or nmol/L, and are not suitable for analysis on the order of mg. In addition, the pretreatment including derivatization is complicated and the working efficiency is decreased. Furthermore, the analysis methods are not a general method because they require a special internal standard substance mainly using 13C for quantitative analysis. Therefore, the conventional methods are not suitable for analysis of functional foods including capsules and the like. These methods have taken no measures against the possible decrease in quantitative performance due to the fact that PQQ is prone to react with many food components and is subject to interference from the components during analysis.

Non-Patent Literature 1 describes a method of derivatizing PQQ with a diamine and subjecting it to absorbance analysis, as a convenient method that enables analysis on the order of mg. However, this method is based on the premise that a sample contains no substance having a specific absorbance other than PQQ, and it does not assume that functional foods containing PQQ and many other coexisting components are measurement objects. That is, absorbance analysis cannot address with the interference from food components, and inexpensive and safe analysis method of derivatization of PQQ analysis has not been known yet.

Non-patent Literature 2 reports a method for suppressing interference during analysis. However, the method includes the step of removing ascorbic acid before performing HPLC analysis to prevent interference from ascorbic acid.

Therefore, no special consideration is given to components other than ascorbic acid, and it cannot sufficiently deal with quantitative analysis of functional foods and the like containing complex and diverse coexisting components.

CITATION LIST

Patent Literatures

Patent Literature 1: Japanese Patent Laid-Open No. 4-145360
Patent Literature 2: Japanese Patent Laid-Open No. 2017-187321

Non-Patent Literature

Non-Patent Literature 1: Tomoki Suizu et al., BUNSEKI KAGAKU Vol. 60, No. 7, pp. 599-602 (2011)
Non-Patent Literature 2: Kazuto Ikemoto et al., BUNSEKI KAGAKU Vol. 65, No. 6, pp. 339-342 (2016)

SUMMARY OF INVENTION

Technical Problems

In consideration of quantitative analysis of functional foods or the like containing complex and diverse coexisting components, among the above methods, the method using HPLC is relatively simple, whereas it has a problem that it is susceptible to interfering substances and is impaired in quantitative performance. It is plausible to derivatize PQQ to solve such problems. The derivatization is generally performed using an esterification, acylation or silylation reaction, but these derivatization reagents are expensive and highly reactive and therefore require safety and handling precautions.

In addition, a PQQ derivative contained on the order of mg in a capsule or the like requires a large amount of derivatization reagent. Therefore, on the premise of providing a more versatile and convenient quantitative analysis method, the use of derivatization reagent mentioned above is not suitable.

The present invention has been made in view of the above problems. An object of the present invention is to provide an analysis method that can determine quantitatively PQQ contained in a measurement object, containing PPQ on the order of mg and many other coexisting components, such as a functional food rapidly and conveniently without being affected by the coexisting components. Another object of the present invention is to provide an analysis method comprising a derivatization step, which is safe, convenient and excellent in handleability when derivatizing PQQ to remove the influence of coexisting components.

Solution to Problems

The present inventors have made intensive studies to solve the above mentioned problems. As a result, they have found that pyrroloquinoline can be analyzed quantitatively by converting pyrroloquinoline quinone into a more stable component, imidazopyrroloquinoline using glycine and determining quantitatively the imidazopyrroloquinoline, thereby solving the above problems, and they have completed the present invention.

In the process, PQQ is prone to reduction, aldol and imination reactions due to its having a quinone structure, and it is therefore subject to interference from reducing substances, amino compounds and aldehyde compounds. To address this, the present inventors have studied a method in which the derivatization has been completed earlier than reactions with the interfering substances and the derivatized substances is not changed by the interfering substances, and in turn, have studied a safer and cheaper reagent that achieve the method. As a result, they have found a suitable method.

In addition, as a more suitable method depending on the dosage form of a measurement object, for example, to analyze PQQ contained in capsules or tablets, the present inventors have studied removing lipid-soluble contaminants by an organic solvent extraction method and adjusting the derivatization reaction conditions and as a result, have found a suitable method. Specifically, the present inventors have found that quantitative performance can be further improved by removing lipid-soluble contaminants using an organic solvent, making the reaction faster than that of a water-soluble interfering substance and derivatizing PQQ more completely by an oxidation step and that quantitative accuracy is enhanced by a standard addition method, and the like. However, these specific methods are means to be more optimized because the analysis method of the present invention is directed to a wide range of measurement objects, and more suitable specific methods are presented to the users of the analysis method of the present invention, but these specific means should not be construed in a limited way as essential means in the present invention.

Accordingly, the present invention is as follows.

[1]

An analysis method comprising:

a sample preparation step of preparing a measurement sample by mixing a measurement object containing pyrroloquinoline quinone or a salt thereof with glycine so that the pyrroloquinoline quinone or the salt thereof reacts with the glycine to produce imidazopyrroloquinoline or a salt thereof; and a quantitative analysis step of determining quantitatively the amount of the pyrroloquinoline quinone and the salt thereof contained in the measurement object, based on a chromatogram of the imidazopyrroloquinoline and the salt thereof contained in the measurement sample obtained by chromatography.

[2]

The analysis method according to [1], where in the sample preparation step, an organic solvent incompatible with water is further mixed to dissolve oil-soluble components in the measurement object in the organic solvent, and the organic solvent is then removed to prepare a measurement sample having the oil-soluble components in the measurement object removed.

[3]

The analysis method according to [1] or [2], further comprising an oxidation step of converting the pyrroloquinoline quinone into its oxidized form, before or during the reaction with the glycine.

[4]

The analysis method according to any one of [1] to [3], wherein the content of the pyrroloquinoline quinone or the salt thereof contained in the measurement object is 0.0001% by mass or more and less than 100% by mass.

[5]

The analysis method according to any one of [1] to [4], wherein the content of the glycine contained in the measurement sample is 1 to 40% by mass.

[6]

The analysis method according to any one of [1] to [5], wherein the content of the glycine contained in the measurement sample is 100 to 1,000,000 times the weight of the pyrroloquinoline quinone or the salt thereof.

[7]

The analysis method according to any one of [1] to [6], further comprising a dilution step of adding a diluent after mixing the measurement object containing the pyrroloquinoline quinone or the salt thereof with the glycine.

[8]

The analysis method according to any one of [1] to [7], wherein a method for the quantitative analysis by the chromatography is a standard addition method.

[9]

The analysis method according to any one of [1] to [8], wherein the measurement object comprises at least one selected from Group A consisting of aspartic acid, glutamic acid, lysine, arginine, histidine, glycine, alanine, valine, leucine, isoleucine, serine, threonine, cysteine, methionine, asparagine, glutamine, proline, phenylalanine, tyrosine, tryptophan, theanine, ascorbic acid, sodium ascorbate, calcium ascorbate, acetylcysteine, collagen, vegetable extracts, glucose and fructose.

[10]

The analysis method according to any one of [1] to [9], wherein the measurement object comprises at least one selected from Group B consisting of edible oils and fats, lipoic acid, DHA, EPA, lecithin, vitamin E, glycerylphosphorylcholine, magnesium stearate, silica, rice flour, cellulose, dextrin, mannitol, xylitol, lactose and cyclodextrin.

Advantageous Effects of Invention

According to the present invention, an analysis method that can quantitatively determine PQQ contained in a measurement object, containing a significant amount of PPQ and many other coexisting components, such as functional foods rapidly and conveniently without being affected by the coexisting components can be provided. According to the present invention, an analysis method comprising a derivatization step, which is safe, convenient and excellent in handleability when derivatizing PQQ to remove the influence of coexisting components can be provided. Thereby, quantitative determination of PQQ in various products including foods can be established in a wide concentration range, and can contribute to the development of health foods, medicines and the like related to PQQ-related compounds.

DESCRIPTION OF EMBODIMENTS

Figure 1:
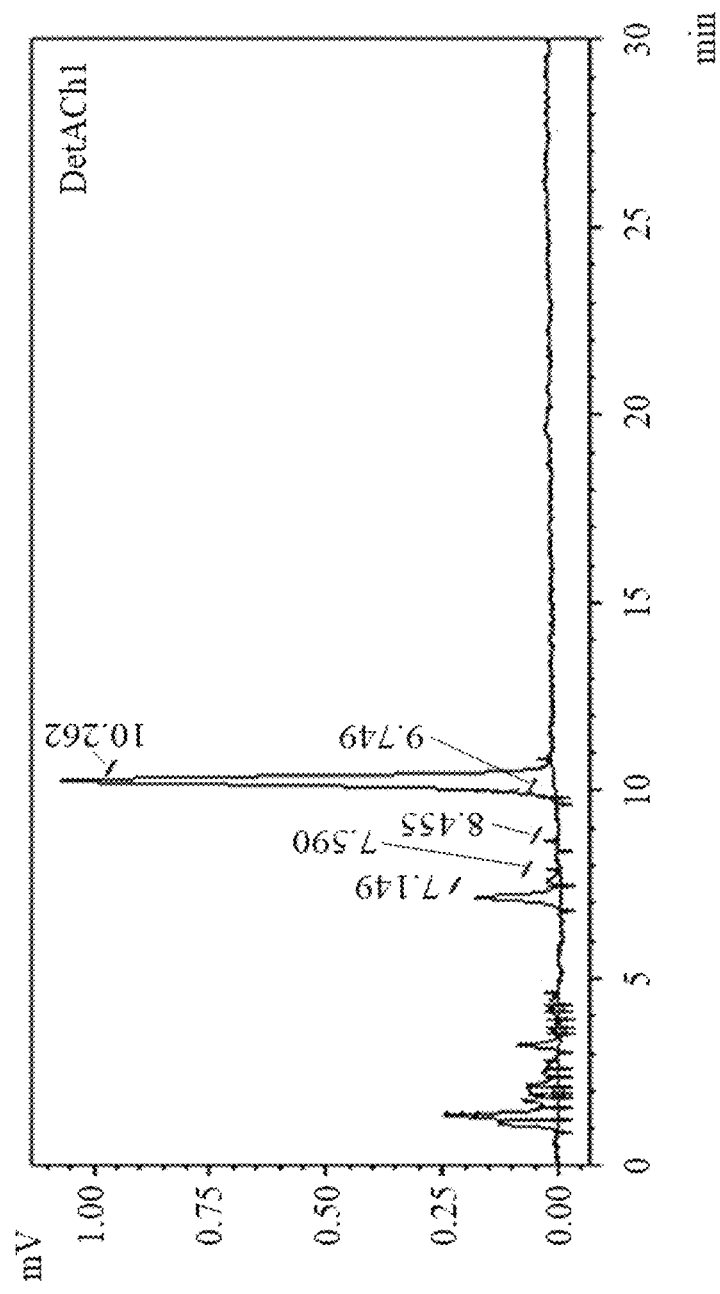
FIG. 1 shows a chromatogram obtained by subjecting a measurement sample to an HPLC analysis in Example 1.

Hereinafter, embodiments of the present invention (hereinafter referred to as "present embodiment") will be described in detail, but the present invention is not limited thereto, and various modifications can be made thereto without departing from the scope of the invention.

[Analysis Method]

An analysis method according to the present embodiment comprises: a sample preparation step of preparing a measurement sample by mixing a measurement object containing pyrroloquinoline quinone or the salt thereof with glycine so that the pyrroloquinoline quinone or the salt thereof reacts with the glycine to produce imidazopyrroloquinoline or a salt thereof; and a quantitative analysis step of determining quantitatively the amount of the pyrroloquinoline quinone or the salt thereof contained in the measurement object, based on a chromatogram of the imidazopyrroloquinoline and the salt thereof contained in the measurement sample obtained by chromatography.

[Sample Preparation Step]

The sample preparation step is a step of preparing a measurement sample by mixing a measurement object containing pyrroloquinoline quinone with glycine so that the pyrroloquinoline quinone or the salt thereof reacts with the glycine to produce imidazopyrroloquinoline or a salt thereof. As used herein, "to produce imidazopyrroloquinoline or a salt thereof" may be, without particularly limited to, any mode in which pyrroloquinoline quinone or a salt thereof reacts with glycine during mixing the measurement object containing pyrroloquinoline quinone with the glycine.

(Analysis Object)

Pyrroloquinoline quinone which is an analysis object in the analysis method of the present embodiment is shown below. PQQ includes an oxidized-type PQQ represented by the following formula (1) and a reduced-type PQQ represented by the following formula (2), and can be in various states varying from the state in which the oxidized-type PQQ is relatively more stable to the state in which the reduced-type PQQ is a relatively more stable, depending on the environment. For example, in a solution where PQQ is prone to be reduced, the reduced-type PQQ is thereby relatively more stable, whereas under an oxidized environment, the oxidized-type PQQ is relatively more stable. In this respect, according to the analysis method of the present embodiment, the total amount of the oxidized-type PQQ and the reduced-type PQQ can be determined quantitatively.

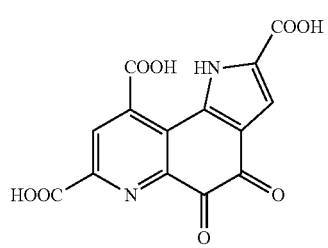

(1)

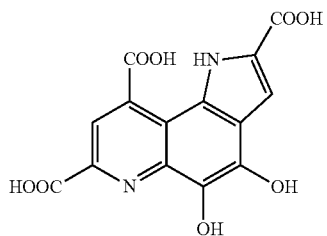

(2)

Examples of the salt of pyrroloquinoline quinone to be analyzed described above include, but not particularly limited to, a salt with a metal such as an alkali metal or an alkaline earth metal, and a salt with a nonmetal such as an ammonium cation. In particular, a disodium salt, which is a kind of alkali metal salt, is widely used in foods and is thereby important as an analysis object.

(Measurement Object)

Examples of the measurement object containing pyrroloquinoline quinone include, but not particularly limited to, a drug or supplement for oral administration in the form of a capsule, a tablet, a powder, a granule and the like; a beverage; a jelly; a gummy candy; and other foods such as a retort food. Additional examples of the measurement object may include a cosmetic, a cleaning agent and other external preparations, which are not a food or drink, and products in general including PQQ. These measurement objects may optionally contain components other than pyrroloquinoline quinone. The optional components include components which do not particularly affect the quantitative analysis of pyrroloquinoline quinone as well as components which interfere with the quantitative analysis of pyrroloquinoline quinone in the conventional method (hereinafter also referred to as "interfering substance"). As interfering substances which can coexist with pyrroloquinoline quinone, compounds of the following Groups A and B are assumed.

The compounds of Group A are compounds that can react with PQQ in a sample preparation step to form unspecified analogs which may interfere with the analysis. Specific examples of the compounds belonging to Group A include essential amino acids such as aspartic acid, glutamic acid, lysine, arginine, histidine, alanine, valine, leucine, isoleucine, serine, threonine, cysteine, methionine, asparagine, glutamine, proline, phenylalanine, tyrosine and tryptophan; derivatives of essential amino acids such as theanine and acetylcysteine; amino acids other than essential amino acids; vitamins and their derivatives such as ascorbic acid, sodium ascorbate and calcium ascorbate; proteins such as collagen; sugars such as glucose and fructose; and extracts of foods such as vegetables, fruits, seeds, spices, herbs, marine products and meats. Among them, vitamins and their derivatives such as ascorbic acid, sodium ascorbate and calcium ascorbate, and derivatives of essential amino acids such as acetylcysteine have a high interfering effect and are prone to interfere with quantification. In contrast, according to the analysis method of the present embodiment, quantitative analysis can be performed without being affected by interference from the compounds of Group A. In the specification of the present application, "without being affected by interference" also includes the case where even if there is any effect of interference, it is within an acceptable error range in the analysis.

On the other hand, the compounds of Group B are compounds that may interfere with the analysis by inhibiting the extraction of PQQ in the sample preparation step. Specific examples of the compounds belonging to Group B include lipid-soluble components and powder components. More specific examples of the compounds belonging to Group B include fats and oils such as edible fats and oils, non-food fats and oils, animal fats and oils and vegetable fats and oils; lipoic acid; lipids such as docosahexaenoic acid (DHA), eicosapentaenoic acid (EPA) and lecithin; fat-soluble vitamins and their derivatives such as vitamin E; glycerylphosphorylcholine and magnesium stearate; sugars and sugar alcohols such as cellulose, dextrin, mannitol, xylitol, lactose and cyclodextrin; inorganic powders such as silica; and organic powders such as rice powder. Among them, the oils and fats have a high interfering effect and are prone to interfere with quantification. In contrast, according to the analysis method of the present embodiment, quantitative analysis can be performed without being affected by interference from the compounds of Group B.

The content of pyrroloquinoline quinone or a salt thereof contained in the measurement object is preferably 0.0001% by mass or more and less than 100% by mass, more preferably 0.0005% by mass or more and less than 100% by mass and still more preferably 0.001% by mass or more and less than 100% by mass. According to the analysis method of the present embodiment, it is possible to conveniently perform quantitative analysis, even if a measurement object contain a relatively large amount of pyrroloquinoline quinone or a salt thereof.

(Object to be Measured)

The imidazopyrroloquinoline (hereinafter also referred to as "IPQ") which is an object to be measured in the analysis method of the present embodiment is shown below. The imidazopyrroloquinoline is a derivative of pyrroloquinoline quinone obtained by reacting pyrroloquinoline quinone with glycine, which is represented by the following formula (3). IPQ is excellent in stability in that differently from PQQ, it does not react with further optional components such as amino acids. In addition, the elution time of IPQ in liquid chromatography is different from PQQ, and the separation of chromatogram peaks is facilitated. In the analysis method of the present embodiment, quantitative analysis can be performed without interference from any components coexisting in the measurement sample, by forming and detecting IPQ.

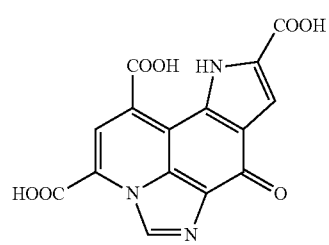

(3)

(Glycine)

By using glycine, the production of IPQ can proceed efficiently and preferentially, and the influence of the above described interfering substances can be eliminated. The form of glycine to be added is not particularly limited, and may be an aqueous solution or powder. When it is in the form of an aqueous solution, a solvent to be used may be water or a buffer.

(Pretreatment)

In a sample preparation step, pretreatment may be performed depending on the form of the measurement object, when mixing the measurement object containing pyrroloquinoline quinone with glycine. The measurement object can be subjected to a suitable treatment so that pyrroloquinoline quinone or a salt thereof and glycine can be easily mixed, such as cutting when the measurement object is a capsule, or crushing when it is a tablet, or the like.

(Liquid Separation Operation)

In a sample preparation step, a measurement sample contains oil-soluble components in the measurement object may be removed by further mixing an organic solvent incompatible with water to dissolve the oil-soluble components in the measurement object in the organic solvent, and then removing the organic solvent (liquid separation operation). In particular, when the measurement object contains fat-soluble components, the quantitative accuracy of PQQ (or IPQ after reaction) tends to be further improved by subjecting the measurement object to liquid separation operation where the lipid-soluble components is extracted in the organic layer and PQQ (or IPQ after reaction) in the aqueous layer. Whether either PQQ or IPQ is extracted in the aqueous layer varies depending on whether the liquid separation operation is performed either after or before reaction of pyrroloquinoline quinone with glycine. When the liquid separation operation is performed during reaction of pyrroloquinoline quinone with glycine, both unreacted PQQ and IPQ produced as a result of reaction may be extracted in the aqueous layer.

Examples of the organic solvent that can be used in the liquid separation operation include, but not particularly limited to, ethyl acetate, chloroform, methylene chloride, cyclohexane, toluene, hexane, dimethylformamide, dimethyl sulfoxide and acetone. Among them, from the viewpoint of low water solubility, the organic solvent is preferably ethyl acetate, chloroform and methylene chloride, and more preferably ethyl acetate having high biodegradability. The liquid separation operation may be omitted when the measurement object is thought not to contain any lipid-soluble component. By performing the liquid separation operation, the quantification accuracy of PQQ (IPQ) tends to be further improved.

(Centrifugation Operation)

When the measurement object contains powder components such as poorly soluble components, it may be subjected to centrifugation operation. The centrifugation operation may be used to separate the aqueous layer and the organic layer during the liquid separation operation.

(Mixing Method)

Examples of the method of mixing a measurement object containing pyrroloquinoline quinone with glycine so that the pyrroloquinoline quinone or the salt thereof reacts with the glycine to produce imidazopyrroloquinoline or a salt thereof include, but not particularly limited to, a method in which pyrroloquinoline quinone or a salt thereof is at least allowed to coexist with glycine in an aqueous solution such as water or a buffer solution.

The conditions are not particularly limited. For example, the temperature and time of the reaction for producing imidazopyrroloquinoline can be varied depending on the sample concentration and the concentrations of the interfering substances. The reaction temperature is preferably 0 to 120° C., more preferably 10 to 90° C. and still more preferably 20 to 80° C. The reaction time is preferably 5 minutes to 2 days, more preferably 10 minutes to 24 hours and still more preferably 10 minutes to 10 hours. The pH of the solution (reaction solution) in which pyrroloquinoline quinone or a salt thereof and glycine coexist is preferably 2 to 12, more preferably 2 to 10 and still more preferably 6 to 8. IPQ in the solution is ionized depending on the pH, which is the same as in case of a dissolved salt.

The amount of glycine to be used is preferably in a large excess with respect to pyrroloquinoline quinone or a salt thereof, and the weight of glycine is preferably 100 to 1,000,000 times, more preferably 200 to 500,000 times and still more preferably 300 to 100,000 with respect to the weight of pyrroloquinoline quinone or a salt thereof.

(Oxidation Step)

From the viewpoint of allowing the reaction for producing imidazopyrroloquinoline to more efficiently proceed, one variation of the mixing method described above preferably comprises an oxidation step of converting pyrroloquinoline quinone into its oxidized form before or during the reaction with glycine. In the oxidation step, a part of reduced-type PQQ can be converted into an oxidized-type PQQ to allow the reaction for producing IPQ to proceed. Examples of the oxidation method in the oxidation step, that is, the method for converting a reduced-type PQQ to an oxidized-type PQQ include, but not particularly limited to, a method in which air is blown into a solution in which pyrroloquinoline quinone or a salt thereof and glycine coexist, and a method of placing a liquid of interest in a container and subjecting it to an operation for fully contacting it with air (mixing it well with air in the container) such as shaking.

One variation of the oxidation method described above may comprise a dilution step of adding a diluent after mixing the measurement object containing pyrroloquinoline quinone with glycine. The diluent is not particularly limited, but a method of adding water or a buffer is included. The buffer is not particularly limited, but it is preferably a carbonate buffer. Such a dilution step cause pyrroloquinoline quinone to be easily converted into its oxidized form and thereby tends to cause the reaction for producing imidazopyrroloquinoline to proceed more efficiently.

In the dilution step described above, an HPLC eluent may be used as a diluent, from the viewpoint of reducing the difference between the sample to be introduced into HPLC and the HPLC eluent in composition and thereby inhibiting the occurrence of shock peak, fluctuation in peak shape and variation in elution time. The diluent to be used for the purpose of converting the above described reduced-type PQQ into the oxidized-type PQQ may be the same as or different from the diluent to be used for the purpose of inhibiting variation due to the shock peak or the like. These diluents different in the purpose of use may be added simultaneously or separately. From the viewpoint of causing the derivatization reaction with glycine to proceed, it is preferable to first add the diluent to be used for the purpose of converting the above described reduced-type PQQ into the oxidized-type PQQ and later add the diluent to be used for the purpose of inhibiting variation due to the shock peak or the like, or alternatively to add them simultaneously. In particular, the later addition of the diluent to be used for the purpose of inhibiting variation due to the shock peak or the like is also referred to as a re-dilution step.

(Measurement Sample)

The measurement sample obtained as described above may include imidazopyrroloquinoline or a salt thereof obtained by reacting pyrroloquinoline quinone or a salt thereof with glycine, unreacted glycine and each of the other components contained in the measurement object.

The content of glycine contained in the measurement sample is preferably 1 to 40% by mass, more preferably 3 to 20% by mass and still more preferably 3 to 10% by mass.

The content of glycine contained in the measurement sample can be thought to be the amount of unreacted glycine contained in the measurement sample, that is, the amount of glycine left after all pyrroloquinoline quinone or a salt thereof is converted to imidazopyrroloquinoline. When the content of glycine is 1% by mass or more, it can be said that pyrroloquinoline quinone or a salt thereof is sufficiently converted to imidazopyrroloquinoline. When the content of glycine is 40% by mass or less, the influence on quantitative measurement of too much glycine contained in the measurement sample tends to be suppressed.

[Quantitative Analysis Step]

A quantitative analysis step is a step of determining quantitatively the amount of the pyrroloquinoline quinone contained in the measurement object, based on a chromatogram of the imidazopyrroloquinoline and the salt thereof contained in the measurement sample obtained by chromatography. As used herein, a chromatogram refers to a chart obtained by plotting the signal of each component obtained for each elution time with the time as the X axis and the signal intensity as the Y axis.

As a quantitative analysis method for imidazopyrroloquinoline and a salt thereof contained in the measurement sample by chromatography, a conventional method can be used, and examples thereof include a standard addition method, an internal standard method and an absolute calibration curve method. The quantitative determination method may be adopted in consideration of the required accuracy and correction, and among them, the standard addition method is preferable from the viewpoint of minimizing the influence of interference and enhancing the analysis accuracy.

The standard addition method that can be used in the present embodiment is the same as a conventional method. Examples of the standard addition method include a method comprising: obtaining a chromatogram of a measurement sample using a detector capable of detecting imidazopyrroloquinoline and a salt thereof; identifying the peak derived from imidazopyrroloquinoline and a salt thereof; and determining quantitatively imidazopyrroloquinoline and a salt thereof contained in the measurement sample from a calibration curve previously determined based on the area of the peak. In construction of a calibration curve, first, a standard solution of imidazopyrroloquinoline having a known concentration is previously prepared, and the standard solution is added to a measurement sample to prepare a sample group for constructing a calibration curve. Then, a chromatogram of the sample group is obtained, the area of the peak derived from imidazopyrroloquinoline and a salt thereof is measured, and a graph is created by plotting the area of the peak measured against the amount of imidazopyrroloquinoline added to the measured sample (the amount of imidazopyrroloquinoline added by the standard solution). An approximate straight line showing the relationship between the area of the peak and the concentration of imidazopyrroloquinoline and a salt thereof is obtained from the plot by the least-squares method or the like, and the calibration curve is constructed based on the approximate straight line.

The type of chromatography that can be used in the present embodiment may be adopted in consideration of the required accuracy and correction, and examples thereof include liquid chromatography (LC) such as high performance liquid chromatography (HPLC). The combination of column and eluent is not particularly limited in the chromatography of interest. The HPLC system comprises a separation column and a pump for feeding a separation solution into the separation column. The HPLC system may comprise other elements such as an autosampler, a heater, a detector for detecting separated components, and the like. Examples of the detector include a UV detector, a fluorescence detector and a mass spectrometer A reverse phase column can be used as the separation column. Examples of the reverse phase column include columns packed with octadecylsilylated silica gel packing material (ODS column, C8 column, C2 column), and columns packed with octadecylsilylated silica gel packing blended with an ion exchange resin, but an ODS column is particularly preferred. Particularly, when HPLC analysis is performed, it is preferable to use a column packed with octadecylsilylated silica gel packing material (ODS column) having a particle size of 5.0 μm or less, and an ODS column packed with octadecylsilylated silica gel packing material having a particle size of 1.7 to 5.0 μm is more preferred.

Examples of the eluent include, but not particularly limited to, a phosphate buffer, an acetate buffer, a formate buffer, a carbonate buffer and a mixed buffer thereof. An organic solvent may be added thereto as needed. Examples of the organic solvent include, but not particularly limited to, acetonitrile and methanol. An ion pair method in which an ion pair reagent is added to the eluent may be also used for the purpose of increasing the degree of separation. Examples of the ion par reagent include, but not particularly limited to, an ammonium salt and a sulfonic acid compound.

Examples of the elution method include, but not particularly limited to, an isocratic elution method in which the composition of a mobile phase (eluent) in a feed liquid is not changed; and a gradient elution method in which the composition of a mobile phase (eluent) in a feed liquid is changed. The elution method can be appropriately selected depending on the separation ability.

The analysis method of the present embodiment has the following advantages and features in a quantitative analysis of PQQ. First, derivatization results in stabilization and thereby less change over time. Second, interference from substances that react with PQQ can be reduced. In addition, glycine, such as glycine to be used for derivatization is inexpensive and safe.

EXAMPLES

Hereinafter, the present invention will be illustrated more specifically with reference to Examples and Comparative Examples. The invention is not limited in any way to the following Examples.

The method of preparing each sample used for analysis is described below. The reagents used in the Examples are Wako special grade reagents, unless indicated otherwise.

(1) 10% Glycine solution: This was prepared by weighing 100 g of glycine and dissolving it in 900 g of distilled water.

(2) Standard Addition Solution (2-1) PQQ Stock solution: An amount of 100 mg of pyrroloquinoline quinone disodium salt (manufactured by Mitsubishi Gas Chemical Company, Inc.; Na/pyrroloquinoline quinone molar ratio 1.70 to 2.10; water content<12%; HPLC purity>99.0%) was dissolved in the 10% glycine solution and the total weight was adjusted to 20 g. The concentration of PQQ in the PQQ stock solution was 5 g/L.

(2-2) 0.1 g/L Addition solution: The PQQ stock solution (2 g) was diluted with the 10% glycine solution, and the total weight was adjusted to 100 g. The concentration of PQQ was 0.1 g/L.

(2-3) 0.2 g/L Addition solution: The PQQ stock solution (4 g) was diluted with the 10% glycine solution, and the total weight was adjusted to 100 g. The concentration of PQQ was 0.2 g/L.

(2-4) 0.3 g/L Addition solution: The PQQ stock solution (6 g) was diluted with the 10% glycine solution, and the total weight was adjusted to 100 g. The concentration of PQQ was 0.3 g/L.

(3) Carbonate Buffer (3-1) 250 mM Carbonate buffer: $Na_2CO_3$ (15.95 g) and $NaHCO_3$ (8.4 g) were dissolved in distilled water and the total volume was adjusted to 1 L.

(3-2) 50 mM Carbonate buffer: This was prepared by diluting the 250 mM carbonate buffer five-fold with water.

(4) Comparison Standard Addition Solution (4-1) PQQ Comparison stock solution: An amount of 100 mg of pyrroloquinoline quinone disodium salt (manufactured by Mitsubishi Gas Chemical Company, Inc.; Na/pyrroloquinoline quinone molar ratio 1.70 to 2.10; water content<12%; HPLC purity>99.0%) was dissolved in the 50 mM carbonate buffer and the total weight was adjusted to 20 g. The concentration of PQQ in the PQQ comparison stock solution was 5 g/L.

(4-2) 0.1 g/L Comparison addition solution: The PQQ comparison stock solution (2 g) was diluted with the 50 mM carbonate buffer, and the total weight was adjusted to 100 g. The concentration of PQQ was 0.1 g/L.

(4-3) 0.2 g/L Comparison addition solution: The PQQ comparison stock solution (4 g) was diluted with the 50 mM carbonate buffer, and the total weight was adjusted to 100 g. The concentration of PQQ was 0.2 g/L.

(4-4) 0.3 g/L Comparison addition solution: The PQQ comparison stock solution (6 g) was diluted with the 50 mM carbonate buffer, and the total weight was adjusted to 100 g. The concentration of PQQ was 0.3 g/L.

(5) HPLC Eluent (100 mM $CH_3COOH$/100 mM $CH_3COONH_4$=30/70 (pH 5.1)):

$CH_3COOH$ (6.0 g) was dissolved in distilled water and the total volume was adjusted to 1 L to prepare 100 mM $CH_3COOH$ (Liquid 1), and separately, $CH_3COONH_4$ (7.71 g) was dissolved in distilled water and the total volume was adjusted to 1 L to prepare 100 mM $CH_3COONH_4$ (Liquid 2). Thereafter, 300 mL of the Liquid 1 and 700 mL of the Liquid 2 were mixed to obtain a buffer to be used as an HPLC eluent and a carbonate buffer. It was confirmed that the pH of the obtained buffer was 5.1±0.2.

(6) Sample diluent solution: The HPLC eluent was used as a sample diluent solution.

[HPLC Analysis Conditions]

Liquid feed unit: LC-10AD (manufactured by Shimadzu Corporation)

Column: YMC-Pack ODS-A (manufactured by YMC CO., LTD.; length: 150 mm; inner diameter: 4.6 mm; particle diameter: 5 μm)

Detector: UV 259 nm

HPLC eluent: described above

Column temperature: 40° C.

Eluent flow rate: 1.5 mL/min

Introduction amount: 3 μL

Analysis time: 30 min

Example 1

Hard Capsule (Sample Preparation Step)

One capsule of a commercially available hard capsule product containing about 5 mg of pyrroloquinoline quinone disodium salt was used as a measurement object. It was described in the label indication for ingredients of the hard capsule product that it contained an enzyme-treated asparagus extract, dextrin, coenzyme Q10, pyrroloquinoline quinone disodium salt, sucrose fatty acid ester, a coloring agent (caramel), silicon dioxide and gelatin.

The shell capsule of the hard capsule product was cut, and the shell capsule and the content of its capsule were all placed in a 50 mL container (centrifuge tube). Thereafter, 5 mL of ethyl acetate and 25 mL of a 10% glycine solution were placed in the container, and were mixed by applying ultrasonic waves thereto for 60 minutes from the outside of the container while shaking and mixing, so that pyrroloquinoline quinone reacted with glycine to produce imidazopyrroloquinoline. Then, the solution after mixing was subjected to centrifugation with a centrifuge to separate it into an aqueous layer and an oil layer (ethyl acetate layer), and only the aqueous layer was collected to obtain a measurement sample.

The 0.2 mL aliquot of the measurement sample was placed in a 50 mL container, and 2 mL of a 250 mM carbonate buffer was added. Then, it was allowed to stand at 70° C. for 1 hour, shaken at room temperature for another 1 hour, and then diluted five-fold with a sample diluent solution (HPLC eluent). The resulting solution was filtered through a filter and subjected to HPLC analysis under the above conditions. FIG. 1 shows a chromatogram thus obtained. The peak observed at the retention time (Rt) between 10 and 11 minutes of the chromatogram was a peak derived from imidazopyrroloquinoline. Then, the value B of the peak area (area of peak) of the peak derived from imidazopyrroloquinoline was calculated. The operation until the calculation of the above peak area was performed three times (a total of three capsules of the hard capsule product as a measurement object were used), and three peak area values B for the peak derived from imidazopyrroloquinoline were obtained.

[Quantitative Analysis Step]

In the same manner as described above except that 25 mL each of a 0.1 g/L addition solution, a 0.2 g/L addition solution or a 0.3 g/L addition solution was used instead of 25 mL of a 10% glycine solution, a chromatogram for each addition of the 0.1 g/L addition solution, the 0.2 g/L addition solution or the 0.3 g/L addition solution was obtained, and the peak area (area of peak) of the peak derived from imidazopyrroloquinoline was calculated from each chromatograph. The operation until the calculation of the above peak area was performed three times in total, and three peak area values of the peak derived from imidazopyrroloquinoline was obtained for each addition of the 0.1 g/L addition solution, the 0.2 g/L addition solution and the 0.3 g/L addition solution, and a total of 9 values were thereby obtained.

Figure 2:
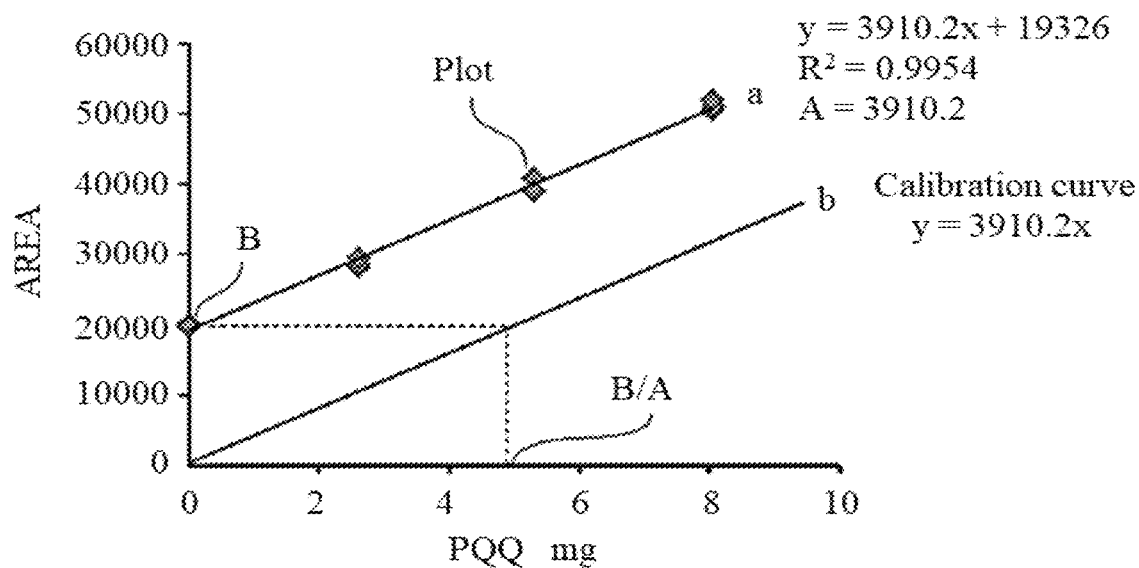
FIG. 2 shows a graph showing a plot of each of the peak area values of IPQ in Example 1 and a straight line a created based thereon as well as a calibration curve b.

Thereafter, the three peak area values of the peak derived from imidazopyrroloquinoline obtained for each addition of the 10% glycine solution, the 0.1 g/L addition solution, the 0.2 g/L addition solution and the 0.3 g/L addition solution (a total of 12 values) were plotted respectively, with the concentration of PQQ as the horizontal axis and the HPLC peak area value as the longitudinal axis; a straight line a was created from the plot by the least-squares method; and the slope A (area/mg) of the straight line a was calculated. Then, a calibration curve b in the standard addition method was constructed. FIG. 2 shows the plot of each of the peak area values and the straight line a created based thereon as well as the calibration curve b.

The hard capsule contains PQQ in an unknown amount of α mg. In this case, the peak area B is shown. FIG. 2 shows a straight line a as a peak area=A (α+addition amount) when PQQ is added thereto. The unknown amount of α mg is represented by α=B/A by plotting the peak area values for varying addition amounts of PQQ to determine A.

Finally, the following equation was applied to each of the three peak area values B to determine the PQQ content of the measurement sample. Table 1 shows the result and their standard deviation and relative standard deviation.

PQQ Content (mg/capsule)=$B$ (area)/$A$ (area/mg)

TABLE 1

| Sample | Slope A (area/mg) | peak area value B (area) | PQQ content (mg/capsule) | Average (mg/capsule) | Standard deviation | Relative standard deviation |
|---|---|---|---|---|---|---|
| 1 | 3910.2 | 20114 | 5.14 | 5.08 | 0.06 | 1.1 |
| 2 | | 19720 | 5.04 | | | |
| 3 | | 19728 | 5.05 | | | |

As can be seen from Table 1, according to the analysis method of the present invention, it was shown that analysis can be performed with less variation and excellent quantitative performance. In Example 1, three peak area values B were measured for comparison in order to confirm the variation, but it was not essential, in the analysis method of the present invention, to measure a plurality of values B of the peak area.

Comparative Example 1

Hard Capsule

The value B of the peak area (area of peak) of the peak derived from pyrroloquinoline quinone was calculated in the same manner as in Example 1 except that a 50 mM carbonate buffer was used instead of 25 mL of a 10% glycine solution and centrifugation with ethyl acetate (separation of water layer and oil layer) was not performed. The slope A (area/mg) was calculated in the same manner as in Example 1 except that a 0.1 g/L comparison addition solution, a 0.2 g/L comparison addition solution or a 0.3 g/L comparison addition solution was used instead of a 0.1 g/L addition solution, a 0.2 g/L addition solution or a 0.3 g/L addition solution. The content of PQQ (mg/capsule) was calculated based on the obtained value B and slope A by the above equation, and a value of 4.54 mg/capsule was thereby obtained as an average value.

The value of 4.54 mg/capsule was less than the value of 5.08 mg/capsule in Example 1. The reason why the value obtained in Comparative Example 1 was less than that in Example 1 was thought because the contaminants contained in the hard capsule (such as contaminants appearing at peaks other than PQQ on the chromatogram, and contaminants not detected at UV 259 nm) interfere with the detection of PQQ. Particularly, considering the label indication for the hard capsule product, it was surmised that the influence of asparagus extract, which is a plant extract, may also be not a little. From the above results, it can be seen that the accurate content can be determined quantitatively by using glycine. If the sample introduced into the HPLC was largely different in composition from the HPLC eluent, shock peak, fluctuation in peak shape and variation in elution time tend to occur, but it was thought that these were also effectively prevented by re-dilution with the HPLC eluent.

Example 2

Soft Capsule (Sample Preparation Step)

A supplement (soft capsule) containing about 10 mg of PQQ marketed by MGC Advanced Chemical Inc. was used as a measurement object. It was described in the label indication for ingredients of the PPQ supplement that it contained edible olive oil, pyrroloquinoline quinone disodium salt, gelatin, vitamin C, glycerin, beeswax and a coloring agent (caramel).

The value B of the peak area (peak area) of the peak derived from imidazopyrroloquinoline and the slope A (area/mg) were calculated in the same manner as in Example 1 except that the above soft capsule was used instead of the hard capsule. The content of PQQ (mg/capsule) was calculated based on the obtained value B and slope A by the above equation, and a value of 10.03 mg/capsule was thereby obtained as an average value.

Comparative Example 2

Soft Capsule

The value B of the peak area (area of peak) of the peak derived from pyrroloquinoline quinone was calculated in the same manner as in Example 2 except that a 50 mM carbonate buffer was used instead of 25 mL of a 10% glycine solution. The slope A (area/mg) was calculated in the same manner as in Example 2 except that a 0.1 g/L comparison addition solution, a 0.2 g/L comparison addition solution or a 0.3 g/L comparison addition solution was used instead of a 0.1 g/L addition solution, a 0.2 g/L addition solution or a 0.3 g/L addition solution. The content of PQQ (mg/capsule) was calculated based on the obtained value B and slope A by the above equation, and a value of 5.5 mg/capsule was thereby obtained as an average value.

The value of 5.5 mg/capsule was about half the value of 10.03 mg/capsule in Example 2. The reason why the value obtained in Comparative Example 2 was less than that in Example 2 was thought because the contaminants contained in the soft capsule (such as contaminants appearing at peaks other than PQQ on the chromatogram, and contaminants not detected at UV 259 nm) interfere with the detection of PQQ. Particularly, considering the label indication for the soft capsule product, it was surmised that the influence of ascorbic acid (vitamin C) may also have a high interfering effect. From the above results, it can be seen that the accurate content can be determined quantitatively even in the presence of ascorbic acid. It was also surmised that the accuracy was improved by eliminating the influence of ascorbic acid (vitamin C) having a relatively high interfering effect, because a reduced-type PQQ was converted into an oxidized-type PQQ by dilution with a carbonate buffer and the reaction for producing IPQ thus easily proceeded. If the sample introduced into the HPLC was largely different in composition from the HPLC eluent, shock peak, fluctuation in peak shape and variation in elution time tend to occur, but it was thought that these were also effectively prevented by re-dilution with the HPLC eluent.

Example 3

Beverage

A liquid obtained by adding 20 mg of pyrroloquinoline quinone disodium to 525 mL of "Namacha" manufactured by Kirin Beverage Company, Limited and allowing it to stand at room temperature overnight was used as a measurement object. Further, for construction of a calibration curve, liquids containing Namacha having 15, 20 and 40 mg of pyrroloquinoline quinone disodium added thereto were prepared, respectively. It was described in the label indication of Namacha that it contained green tea, fresh tea leaf extract and vitamin C.

Namacha (2 mL) after allowed to stand was placed in a 50 mL container, and 0.3 g of powdered glycine was added thereto. Thereafter, ultrasonic waves were applied thereto for 15 minutes from the outside of the container to dissolve all the powdered glycine. It was further shaken for 4 hours, filtered through a filter and subjected to HPLC analysis under the above conditions. The value B of the peak area (area of peak) of the peak derived from imidazopyrroloquinoline and the slope A (area/mg) were calculated. The content of PQQ (mg/capsule) was calculated based on the obtained value B and slope A by the above equation, and a value of 20 mg/capsule was thereby obtained as an average value.

Comparative Example 3

Beverage

HPLC analysis was performed in the same manner as in Example 3 except that powdered glycine was not added. However, the PQQ peak areas for addition of 20 mg of PQQ and addition of 40 mg of PQQ were almost the same values. This indicate that when glycine was not added, the concentration dependence of PQQ contained in the beverage could not be confirmed from the peak area of PQQ. It was surmised that this was because ascorbic acid and green tea which was a plant extract interfere with detection.

Example 4

Influence of Coexisting Substances

Pyrroloquinoline quinone disodium salt (1 g) and 9 g of dextrin were mixed in powder forms. The resulting powder (50 mg) was placed in a 50 mL container, and 50 mg of each of Substance 1 and Substance 2 shown in Table 2 were added thereto and mixed in powder forms. Next, 5 mL of ethyl acetate and 25 mL of a 10% glycine solution were placed in the container and were mixed by applying ultrasonic waves thereto for 30 minutes from the outside of the container while shaking and mixing, so that pyrroloquinoline quinone reacted with glycine to produce imidazopyrroloquinoline. Then, the solution after mixing was subjected to centrifugation with a centrifuge to separate it into an aqueous layer and an oil layer (ethyl acetate layer), and only the aqueous layer was collected to obtain a measurement sample.

The 2 mL aliquot of the measurement sample was placed in a 15 mL container, then allowed to stand at 70° C. for 1 hour and shaken at room temperature for another 1 hour. Thereafter, it was diluted five-fold with a sample diluent solution (HPLC eluent). The resulting measurement sample was subjected to HPLC analysis. Disappearance of the peak derived from PQQ and generation of the peak derived from IPQ were confirmed, and whether or not the derivatization reaction of PQQ to IPQ with glycine proceeded in the presence of the coexisting substances (Substances 1 and 2) was thereby confirmed. The sample in which the derivatization reaction had completely proceeded was rated as A, and the sample in which interference from the coexisting substances was significantly observed was rated as B. The following Table 2 shows the results about the use of the Substances 1 and 2 in combination, but substantially the same tendency was observed when using either Substance 1 or 2 alone.

TABLE 2

| Substance 1 | Substance 2 | Result |
|---|---|---|
| Arginine | Aspartic acid | A |
| Aspartic acid | Aminobutyric acid | A |
| Phenylalanine | Leucine | A |
| Methionine | Tyrosine | A |
| Valine | Cysteine | A |
| Ascorbic acid | Arginine | A |

It was confirmed that the derivatization of PQQ to IPQ proceeded selectively and predominantly by using glycine even if amino acids which coexisted and interfered with PQQ were present.

Example 5

Analysis Range

In the same manner as a 0.1 g/L addition solution or the like, a 0.5 g/L addition solution, a 1.0 g/L addition solution, a 2.0 g/L addition solution, a 3.0 g/L addition solution and a 4.0 g/L addition solution were prepared. The measurement object was not particularly used, and the 0.1 to 4.0 g/L addition solutions were diluted five-fold with a sample diluent solution (HPLC eluent). Each of the resulting solution was filtered through a filter and subjected to HPLC analysis under the above conditions.

Figure 3:
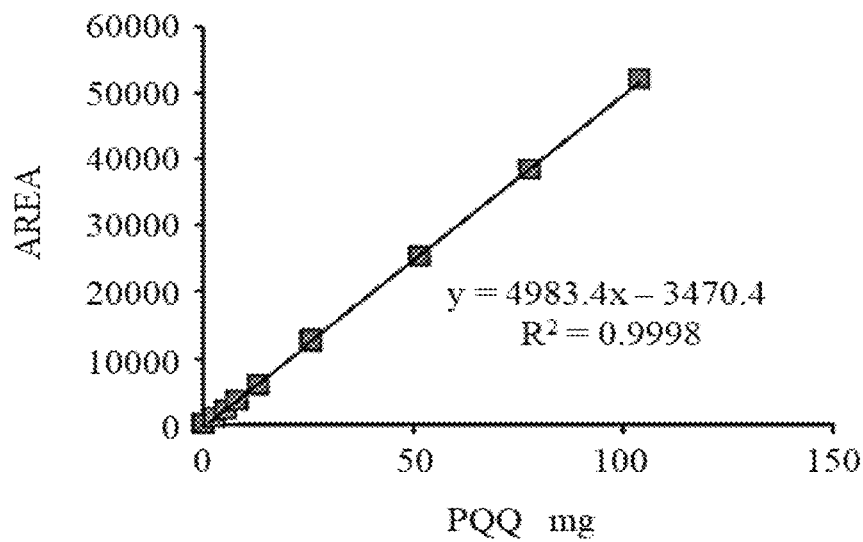
FIG. 3 shows a graph showing a plot of each of the peak area values of IPQ in Example 5 and a straight line c created based thereon.

The peak area (area of peak) of the peak derived from imidazopyrroloquinoline was calculated for each of the addition solutions. Each of the peak area values of the peak derived from imidazopyrroloquinoline was plotted with the concentration of PQQ as the horizontal axis and the HPLC peak area value as the longitudinal axis, and a straight line c was created from the plot by the least-squares method. FIG. 3 shows the plot of each peak area value and a straight line c created based thereon. The fact that the linearity of the straight line c was kept from a high concentration to a low concentration in the standard addition method was one indicator for securing the accuracy of the analysis method of the present invention. As shown in FIG. 3, the linearity was confirmed in the range of 2.5 mg to 100 mg according to the analysis method of the present invention. This indicates that analysis can be performed in a wider concentration range by combining an increase in the addition amount and the dilution operation.

The present application is based on Japanese Patent Application (Japanese Patent Application No. 2018-003636) filed to the Japan Patent Office on Jan. 12, 2018, the contents of which are incorporated herein by reference.

INDUSTRIAL APPLICABILITY

The analysis method of the present invention has industrial applicability as a quantitative measurement method of PQQ contained in food and the like.

The invention claimed is:
1. An analysis method comprising:
a sample preparation step of preparing a measurement sample by mixing a measurement object comprising pyrroloquinoline quinone or a salt thereof with glycine so that the pyrroloquinoline quinone or the salt thereof reacts with the glycine to produce imidazopyrroloquinoline or a salt thereof; and
a quantitative analysis step of determining quantitatively an amount of the pyrroloquinoline quinone or the salt thereof comprised in the measurement object, based on a chromatogram of the imidazopyrroloquinoline or the salt thereof comprised in the measurement sample obtained by chromatography.
2. The analysis method of claim 1, where in the sample preparation step, an organic solvent incompatible with water is further mixed to dissolve oil-soluble components in the measurement object in the organic solvent, and the organic solvent is then removed to prepare a measurement sample having the oil-soluble components in the measurement object removed.
3. The analysis method of claim 1, further comprising an oxidation step of converting the pyrroloquinoline quinone into its oxidized form, before or during the reaction with the glycine.
4. The analysis method of claim 1, wherein a content of the pyrroloquinoline quinone or the salt thereof comprised in the measurement object is 0.0001% by mass or more and less than 100% by mass.
5. The analysis method of claim 1, wherein a content of the glycine comprised in the measurement sample is 1 to 40% by mass.
6. The analysis method of claim 1, wherein a content of the glycine comprised in the measurement sample is 100 to 1,000,000 times a weight of the pyrroloquinoline quinone or the salt thereof.
7. The analysis method of claim 1, further comprising adding a diluent after mixing the measurement object comprising the pyrroloquinoline quinone or the salt thereof with the glycine.
8. The analysis method of claim 1, wherein a method for the quantitative analysis by the chromatography is a standard addition method.
9. The analysis method of claim 1, wherein the measurement object comprises at least one selected from the group consisting of aspartic acid, glutamic acid, lysine, arginine, histidine, glycine, alanine, valine, leucine, isoleucine, serine, threonine, cysteine, methionine, asparagine, glutamine, proline, phenylalanine, tyrosine, tryptophan, theanine, ascorbic acid, sodium ascorbate, calcium ascorbate, acetylcysteine, collagen, vegetable extracts, glucose and fructose.

10. The analysis method of claim 1, wherein the measurement object comprises at least one selected from the group consisting of edible oils and fats, lipoic acid, DHA, EPA, lecithin, vitamin E, glycerylphosphorylcholine, magnesium stearate, silica, rice flour, cellulose, dextrin, mannitol, xylitol, lactose and cyclodextrin.

* * * * *